US00PP35873P2

(12) United States Plant Patent
Gray

(10) Patent No.: US PP35,873 P2
(45) Date of Patent: Jun. 18, 2024

(54) ***CANNABIS* PLANT NAMED 'D1118'**

(50) Latin Name: ***Cannabis* hybrid**
Varietal Denomination: D1118

(71) Applicant: Dewey Scientific, Pullman, WA (US)

(72) Inventor: Michael Rennie Gray, Pullman, WA (US)

(73) Assignee: DEWEY SCIENTIFIC, Pullman, WA (US)

( * ) Notice: Subject to any disclaimer, the term of this patent is extended or adjusted under 35 U.S.C. 154(b) by 2 days.

(21) Appl. No.: 18/189,113

(22) Filed: Mar. 23, 2023

(51) Int. Cl.
*A01H 6/28* (2018.01)
*A01H 5/02* (2018.01)

(52) U.S. Cl.
USPC ..... Plt./258

(58) Field of Classification Search
USPC ..... Plt./258
See application file for complete search history.

(56) References Cited

U.S. PATENT DOCUMENTS

2023/0189677 P1 6/2023 Baasch

OTHER PUBLICATIONS

Allbud, (2023). "Jamaican Chocolate Marijuana Strain," available online at <https://www.allbud.com/marijuana-strains/sativa-dominant-hybrid/jamaican-chocolate>, 3 pages.
Allbud, (2023). "Mango Sherbet Marijuana Strain" available online at <https://www.allbud.com/marijuana-strains/indica-dominant-hybrid/mango-sherbet>, 3 pages.
Bautista et al., (2021). "Flavonoids in *Cannabis sativa*: Biosynthesis, Bioactivities, and Biotechnology," ACS Omega, 6(8):5119-5123.
Booth et al., (2017). "Terpene synthases from *Cannabis sativa*," Plos One, 12(3):e0173911, 20 pages.
Growdiaries, (2023). "Green Point Seeds: Purple Tahoe," available online at <https://growdiaries.com/seedbank/greenpointseeds/purple-tahoe>, 4 pages.
Kovalchuk et al., (2020). "The genomics of cannabis and its close relatives," Annu. Rev. Plant Biol., 71:713-739.
Leafly, (2023). "G13," available online at <https://www.leafly.com/strains/g-13>, 6 pages.
Leafly, (2023). "Memory Loss," available online at <https://www.leafly.com/strains/memory-loss>, 6 pages.
Leafly, (2023). "Passionfruit Haze—14G Premium Flower," available online at <https://www.leafly.com/brands/west-coast-cure/products/west-coast-cure-passionfruit-haze-14g-premium-flower-flower>, 4 pages.
Leafly, (2023). "Purple Punch," available online at <https://www.leafly.com/strains/purple-punch>, 7 pages.
Leafly, (2023). "Trainwreck," available online at <https://www.leafly.com/strains/trainwreck>, 5 pages.
Mihalyov et al., (2021). "Discovery and Genetic Mapping of PM1, a Powdery Mildew Resistance Gene in *Cannabis sativa L.*," Frontiers in Agronomy, 3:720215, 10 pages.
Zager et al., (2019). "Gene Networks Underlying Cannabinoid and Terpenoid Accumulation in *Cannabis*," Plant Physiology, 180(4):1877-1897.
Unpublished U.S. Appl. No. 18/189,956, filed Mar. 24, 2023, titled "*Cannabis* Plant Named 'D1117'," (Copy not submitted herewith pursuant to the waiver of 37 C.F.R. § 1.98(a)(2)(iii)).
Unpublished U.S. Appl. No. 18/189,958, filed Mar. 24, 2023, titled "*Cannabis* Plant Named 'D586'," (Copy not submitted herewith pursuant to the waiver of 37 C.F.R. § 1.98(a)(2)(iii)).

*Primary Examiner* — Karen M Redden
(74) *Attorney, Agent, or Firm* — Morrison & Foerster LLP

(57) ABSTRACT

A new and distinct variety of *Cannabis* plant named 'D1118', characterized by its aroma, its vigor, its deep dark purple flower and leaf tissue, the unique calyx formation of its flowers, and its resistance to powdery mildew, is disclosed.

7 Drawing Sheets

Botanical classification: *Cannabis* hybrid.

Varietal denomination: The varietal denomination of the claimed variety of *Cannabis* plant is 'D1118',

BACKGROUND OF THE INVENTION

*Cannabis* plants have been cultivated for medicinal and recreational purposes for thousands of years. The annual, upright, flowering plants with palmately compound leaves are historically classified into two species. Following this classification, *Cannabis saliva* is tall with long internodes and narrow leaflets, while the shorter, conical *Cannabis indica* is densely branched with broad leaflets. New species classifications have been proposed to address the increased production of *Cannabis* varieties which display features of both historical species, but none have been commonly accepted. Thus, most *Cannabis* varieties sold in the U.S. today continue to be classified as *Cannabis indica, Cannabis saliva*, or *Cannabis* hybrid.

Commercial varieties of *Cannabis* contain floral calyxes and bracts with abundant trichomes. Some types of these hair-like structures (generally referred to as glandular trichomes) secrete cannabinoids and terpenoids, which account for the medicinal and/or psychoactive properties of the plant. Mixtures of these compounds may be separated from the flowers in the form of an oil or resin. Alternatively, the flower buds may be collected and dried to produce marijuana.

Each variety of the *Cannabis* plant has a distinct profile of various cannabinoids and terpenoids that determine its medicinal and/or psychoactive properties. Some varieties have shown potential to relieve nausea, pain, seizures, anxiety, arthritis, and many other medical conditions, with limited psychoactive effects. Other varieties contain high levels of compounds that contribute to dizziness, grogginess, or disorientation. Uplifting or energizing effects have also been observed in some varieties.

*Cannabis* plants present a wide range of potential uses, each requiring a different chemical profile. High or low levels of certain medicinal and/or psychoactive compounds may be desirable for different intended uses. There is therefore a need for new *Cannabis* varieties with new chemical profiles and/or improved characteristics including pest or disease resistance and/or increased yields and/or improved cannabinoid potency.

SUMMARY OF THE INVENTION

In order to meet these needs, the present invention is directed to an improved variety of *Cannabis* plant. In particular, the present invention relates to a new and distinct *Cannabis* hybrid designated as 'D1118'.

*Cannabis* plant variety 'D1118' was derived from a cross between the female plant 'Jamaican Chocolate' (unpatented) and the male plant 'Passion Fruit Haze' (unpatented) in Los Angeles, CA, USA in April of 2021. The original plant of 'D1118' was first asexually propagated via clonal propagation in Los Angeles, CA, USA in November of 2021.

Subsequent asexual propagation of 'D1118' was conducted by clonal propagation. 'D1118' has undergone testing under greenhouse conditions with supplemental lighting and indoor conditions with full lighting in Los Angeles, CA, USA and Pullman, WA, USA for 15 months. 'D1118' has been found to be stable and reproduce true to type through successive generations of asexual propagations via clonal propagation of apical and side shoots.

'D1118' was particularly selected for its unique aroma, vigor, trichome density, a deep dark purple flower coloration that appears near black, and the unique calyx structure of its flowers.

BRIEF DESCRIPTION OF THE DRAWINGS

This new *Cannabis* plant variety is illustrated by the accompanying photographs. The colors shown are as true as can be reasonably obtained by conventional photographic procedures. Plants were initially grown in 2 gallon containers for 10-13 days under an 18 hour light/6 hour dark cycle, then moved to a 12 hour light/12 hour dark lighting regime. Leaves were removed from the plants every 17 days during the flower cycle. Photos were taken 8 weeks after the change in lighting regime.

DETAILED BOTANICAL DESCRIPTION

Figure 1:
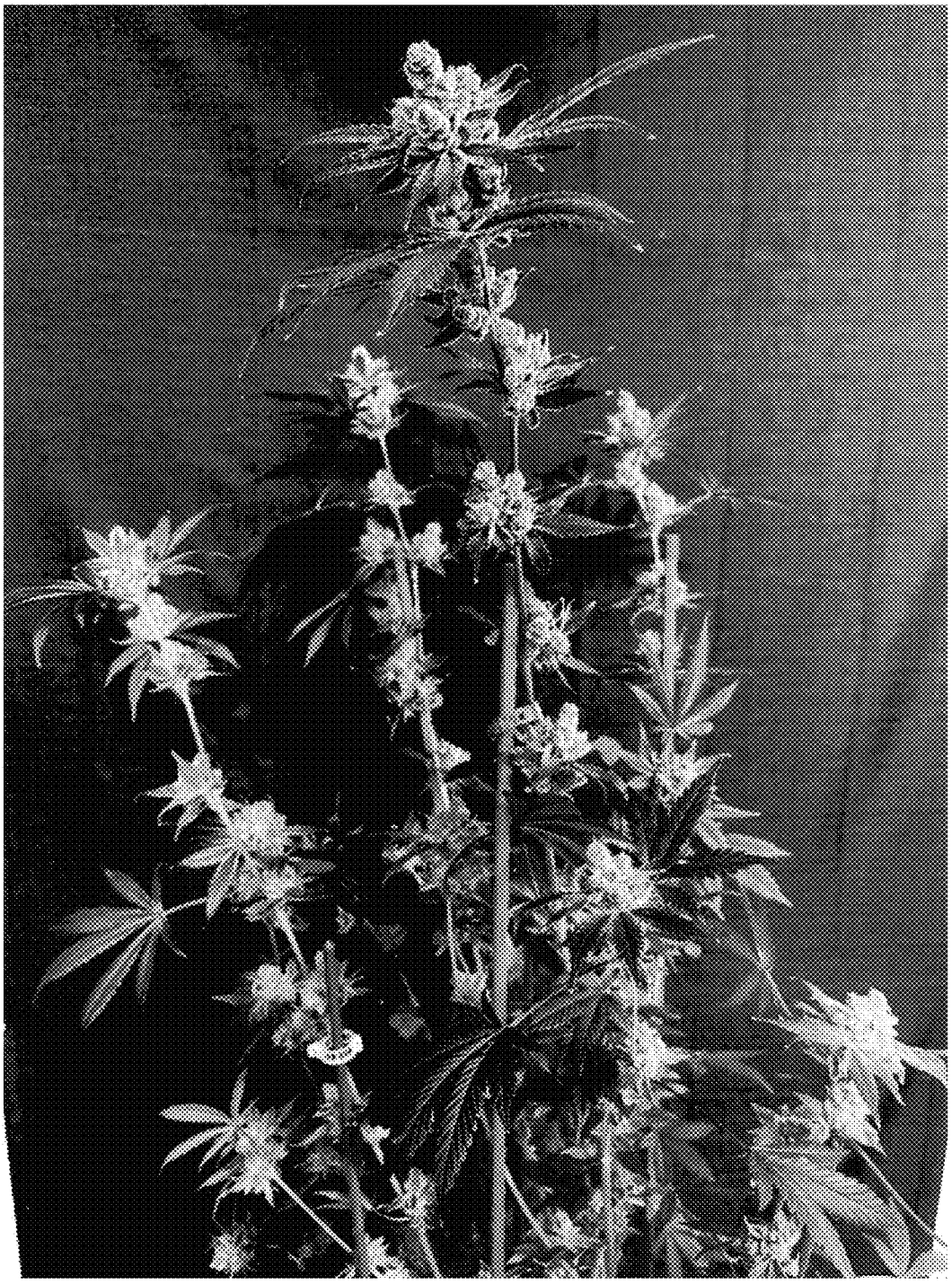
FIG. 1 illustrates a side view of a 'D1118' plant.
Figure 2:
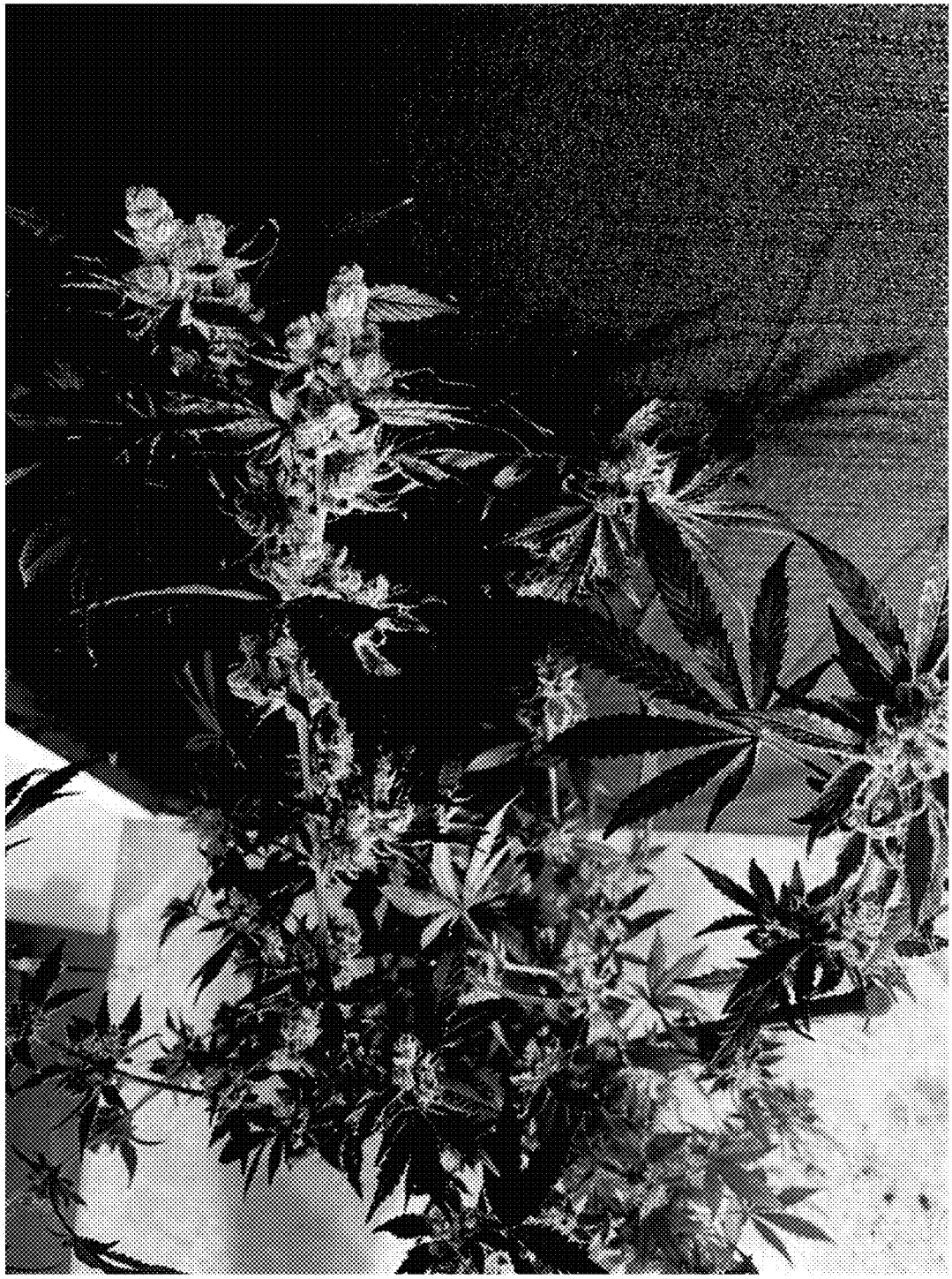
FIG. 2 illustrates a top view of a whole 'D1118' plant.
Figure 3:
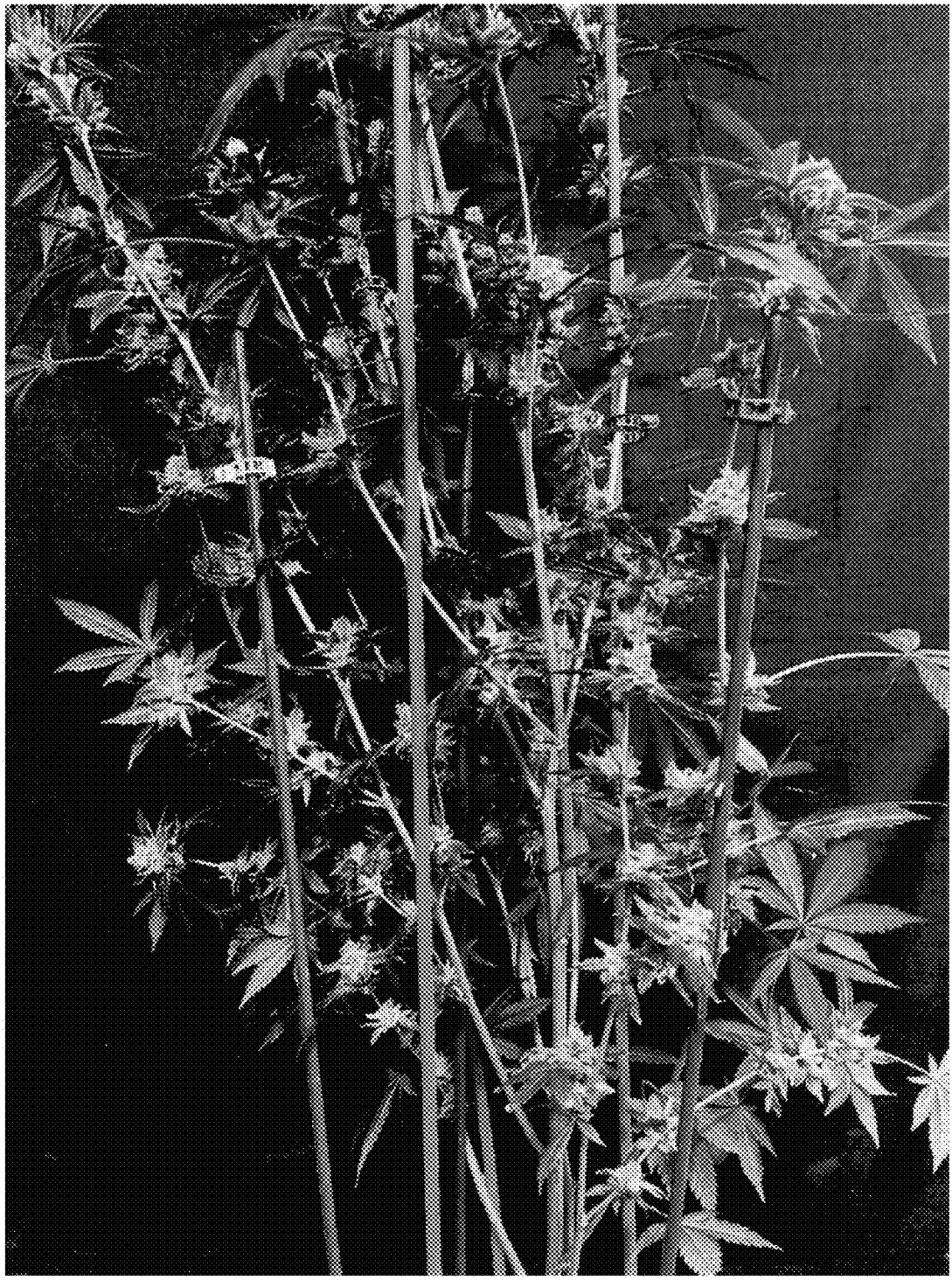
FIG. 3 illustrates branching patterns of a 'D1118' plant.
Figure 4:
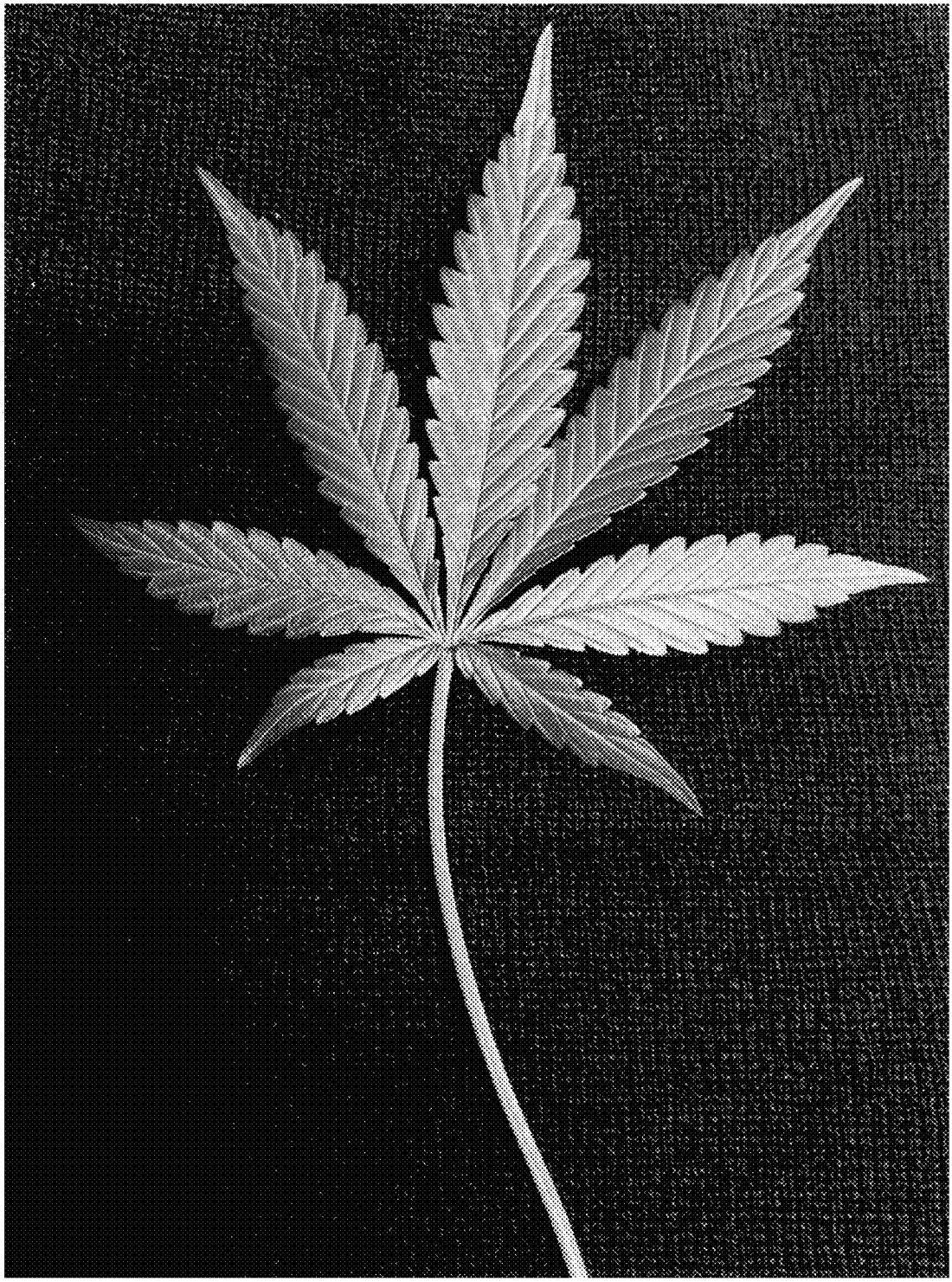
FIG. 4 illustrates the leaf shape of a 'D1118' plant.
Figure 5:
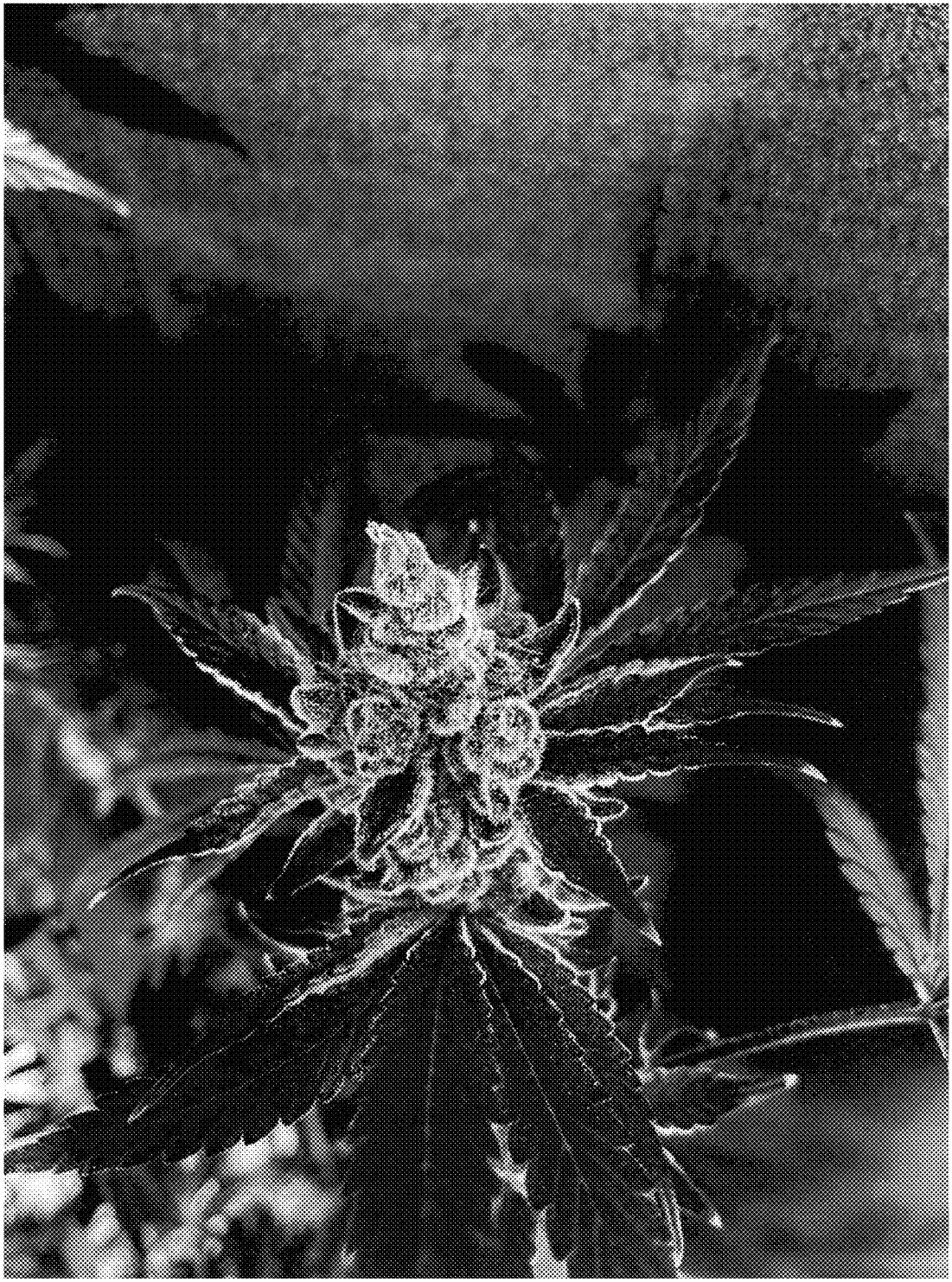
FIG. 5 illustrates a top view of a flower of a 'D1118' plant.
Figure 6:
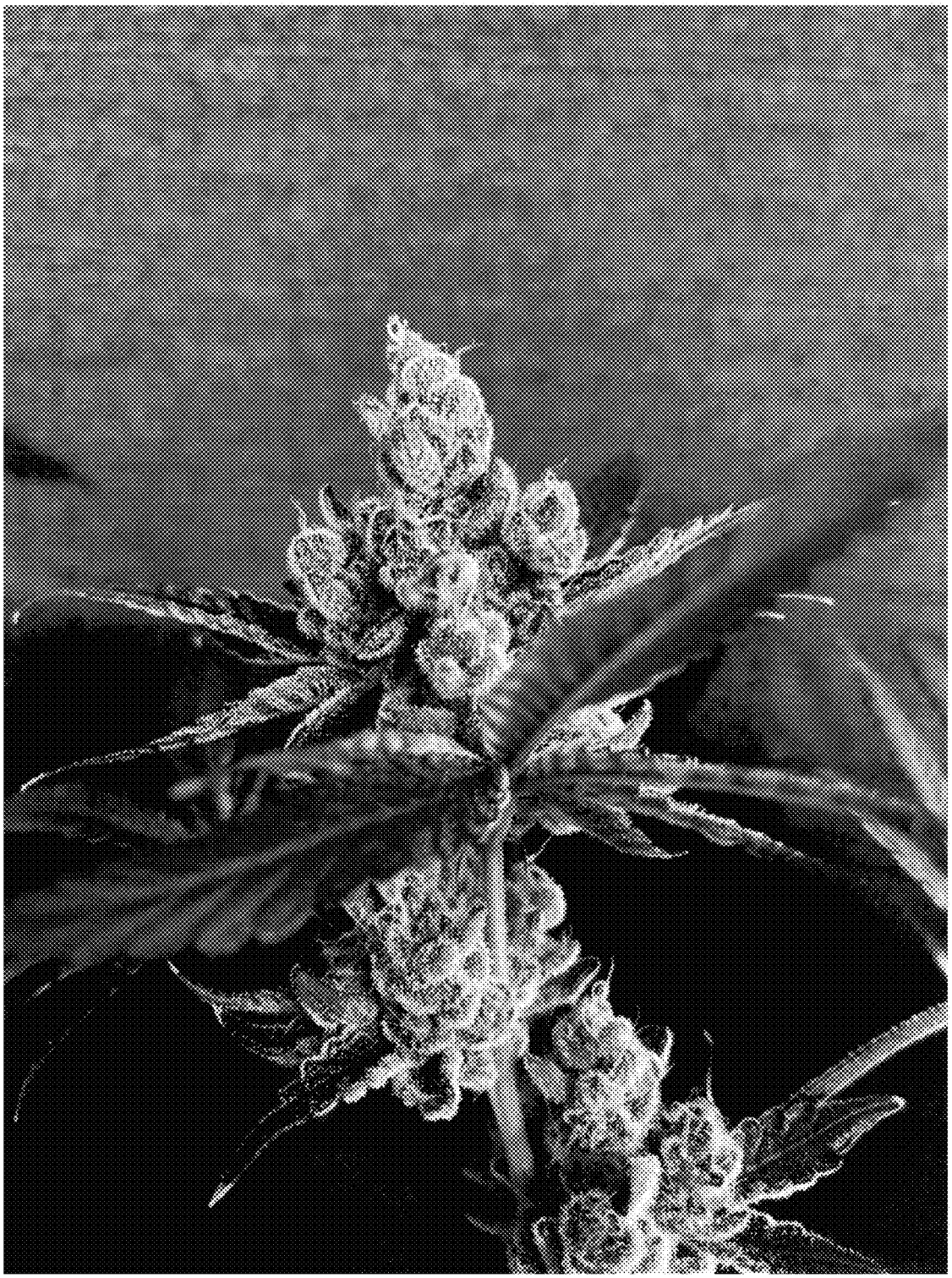
FIG. 6 illustrates a close-up side view of a flower of a 'D1118' plant.
Figure 7:
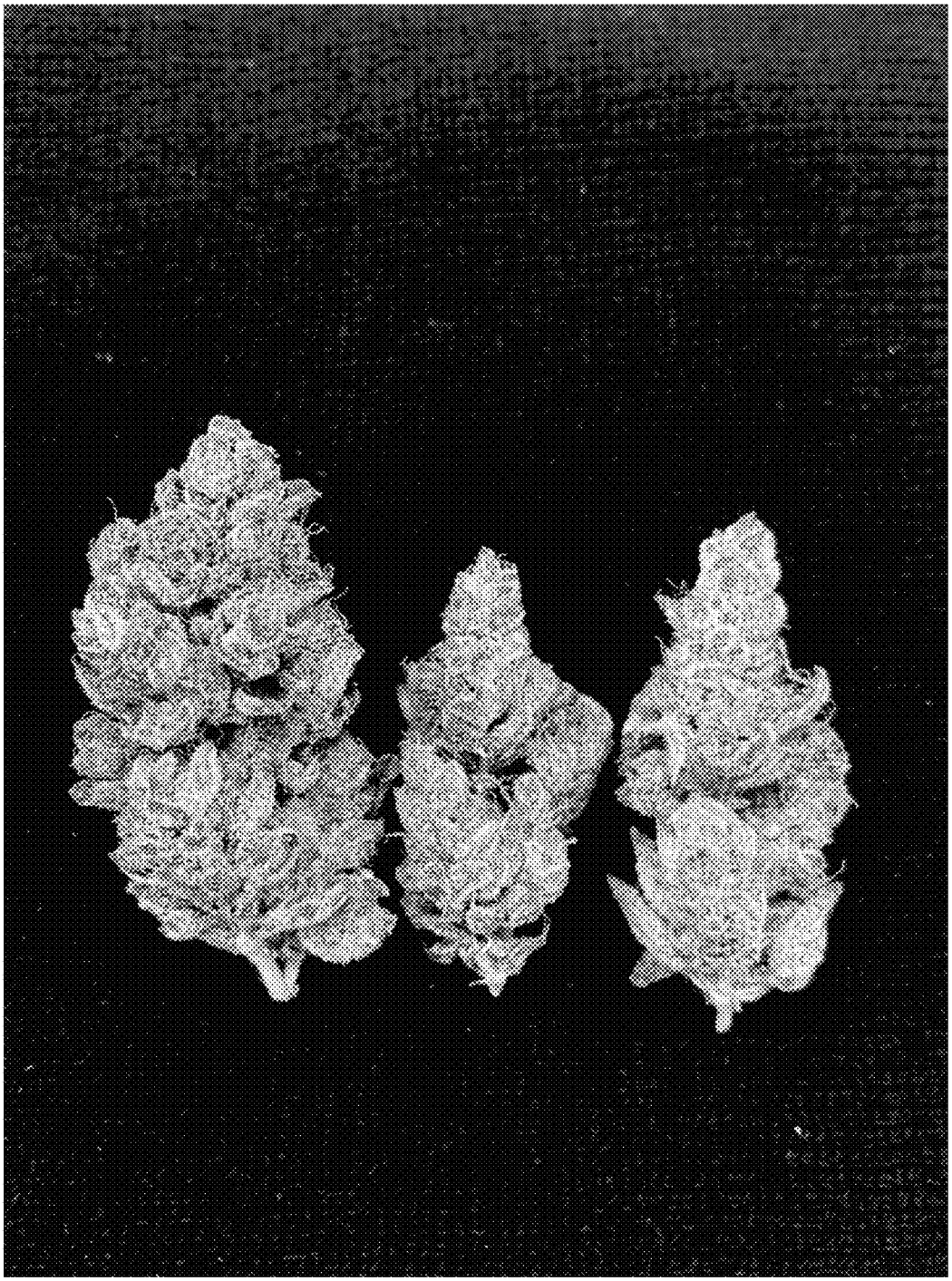
FIG. 7 illustrates dried flower buds of a 'D1118' plant.

The following description sets forth the distinctive characteristics of 'D1118'. The data that define these characteristics are based on observations taken from plants grown in greenhouses in Pullman, WA, USA from June 2022 to September 2022. The growth conditions were as follows (averages and standard deviation for 9 weeks of growth): temperature of 78±5 F (day) and 68±7 F (night); relative humidity of 60±9% (day) and 64±7% (night). Color designations, color descriptions, and other phenotypical descriptions may deviate from the stated values and descriptions depending upon variation in environmental, seasonal, climatic, and cultural conditions. 'D1118' has not been observed under all possible environmental conditions. The indicated values represent averages calculated from measurements of 180 plants after 2 growing cycles, unless otherwise indicated. Color references are primarily provided in hexadecimal code, also known as hex color code, hex code, or HTML color code. Hexadecimal code is understood in the art and follows defined rules as described in, for example, history-computer[dot]com/hex-code-html-color-codes and codeconquest[dot]com/hex-color-codes. Descriptive terminology follows the *Plant Identification Terminology, An Illustrated Glossary,* 2$^{nd}$ edition by James G. Harris and Melinda Woolf Harris, unless where otherwise defined.

Classification:
- *Family*.—Cannabaceae.
- *Species*.—*Cannabis* hybrid.
- *Denomination*.—'D1118'.

Parentage:
- *Female parent*.—'Jamaican Chocolate' (unpatented).
- *Male parent*.—'Passion Fruit Haze' (unpatented).

Propagation:
- *Propagation method*.—Clonal.
- *Time to produce a rooted young plant*.—15 days.

Plant (at flowering stage):
- *Height*.—123 cm.
- *Width*.—71 cm.
- *Vigor*.—Strong.
- *Branching*.—Medium to strong.
- *Branching angles*.—42° (averaged from 3 branches per plant from 3 plants).
- *Intensity of anthocyanin coloration of crown* (*where stem meets roots*).—Absent.
- *Proportion of hermaphrodite plants*.—Low to zero in optimal growing conditions.
- *Proportion of male plants*.—Low to zero in optimal growing condition.

Stem (at flowering):
- *Height*.—111 cm.
- *Diameter at base*.—1.9 cm.
- *Color*.—#C2C76F (yellow green).
- *Depth of ribs or grooves*.—Shallow.
- *Texture*.—Smooth.
- Internode length.—4.9±1.4 cm (average±standard deviation, n=11 internodes from main stem of a total of 3 plants).
- *Number of internodes*.—11 (averaged over multiple plants).
- *Amount of pith in main stem cross-section*.—Thick.
- *Stem trichome type*.—Cystolithic (nonglandular).

Fan leaves (at flowering stage):
- *Length*.—13 cm (includes petiole).
- *Width*.—6.7 cm.
- *Texture on upper surface*.—Smooth.
- *Texture on lower surface*.—Veined.
- *Shape*.—Palmately compound.
- *Margin*.—Serrate.
- *Vein color*.—#EBF9C3 (pale green).
- *Color on upper side*.—#6C5255 (purplish brown) and #292728 (near-black purple).

*Color on lower side*.—#C1CC9A (pale olive green) and #D1BCB7 (pale dusky pink).
*Number of leaflets*.—7.
*Leaflet margin*.—Serrate.
*Leaflet shape*.—Lanceolate.
*Leaflet apex shape*.—Attenuate.
*Leaflet base shape*.—Attenuate.
*Central leaflet length*.—7.63 cm.
*Central leaflet width*.—2.0 cm.
*Trichome types*.—Glandular — Capitate stalked. Nonglandular — Cystolithic.
*Immature trichome color*.—#FFF9E3 (clear/white).
*Mature trichome color*.—#A76426 (amber/brown).

Petiole (at flowering stage):
*Length*.—25.6 mm.
*Diameter*.—1.67 mm.
*Color*.—#B9998F (brownish pink).
*Intensity of anthocyanin coloration*.—Strong.
*Anthocyanin coloration*.—#B8927D (pale pinkish brown).
*Stipule color*.—#B9998F (brownish pink).
*Stipule shape*.—Acicular.
*Stipule size*.—5.25 mm.
*Trichome type*.—Nonglandular — Cystolithic.

Sugar leaves:
*Length*.—2.2 cm.
*Width*.—1.8 cm.
*Texture on upper surface*.—Smooth.
*Texture on lower surface*.—Veined.
*Shape*.—Palmately compound.
*Margin*.—Serrate.
*Vein color*.—#EBF9C3 (pale green).
*Color on upper side*.—#81BA12 (light green) and #3B3236 (dark purple).
*Color on lower side*.—#C1CC9A (pale olive green) and #D1BCB7 (pale dusky pink).
*Number of leaflets*.—5.
*Leaflet margin*.—Serrate.
*Leaflet shape*.—Lanceolate.
*Leaflet apex shape*.—Attenuate.
*Leaflet base shape*.—Attenuate.
*Central leaflet length*.—2.2 cm.
*Central leaflet width*.—0.8 cm.
*Trichome type*.—Glandular — Capitate stalked.
*Immature trichome color*.—#FFF9E3 (clear/white).
*Mature trichome color*.—#A76426 (amber/brown).

Flowers (at flowering stage):
*Flowers per plant*.—2,500-3,000.
*Compound flower density*.—Very dense.
*Flower length*.—32 mm.
*Flower diameter*.—27.67 mm.
*Color*.—Mature flower: #433E35 (Dark purple-brown). Trichomes: #E1E4BA (pale yellow green) and #CDBDAA (pale greyish brown).
*Aroma*.—Chocolate, liquorish, pepper.
*Shape*.—Small purple bract enclosing the ovary with two slender stigmas, without petals or sepals.
*Calyx structure*.—Large, oblong.
*Trichome density*.—Very dense.
*Flowering period*.—9 weeks.
*Bract length*.—7.0 mm.
*Bract width*.—6.5 mm.
*Bract shape*.—Acuminate.
*Average number of bracts per compound flower*.—14.
*Bract color*.—#433E35 (Dark purple-brown).
*Bract trichome type*.—Glandular — Capitate stalked.
*Immature bract trichome color*.—#FFF9E3 (clear/white).
*Mature bract trichome color*.—#A76426 (amber/brown).
*Bracteole length*.—7.0 mm.
*Bracteole width*.—3.25 mm.
*Bracteole shape*.—Acuminate.
*Average number of bracteoles per compound flower*.—28.
*Bracteole color*.—#433E35 (Dark purple-brown).
*Bracteole trichome type*.—Glandular — Capitate stalked.
*Immature bracteole trichome color*.—#FFF9E3 (clear/white).
*Mature bracteole trichome color*.—#A76426 (amber/brown).
*Average number of stigmas per compound flower*.—28.
*Stigma length*.—9.9 mm.
*Immature stigma color*.—#EBCB90 (light yellow).
*Mature stigma color*.—#DEAA68 (orange).
*Stigma trichome types*.—Glandular — Capitate stalked. Nonglandular — Cystolithic.
*Stigma trichome color*.—Clear/white.

Chemotypic characteristics:
*Method of determination*.—HPLC as described in Zager et al. (2019, Plant Physiol. 180(4): 1877-1897).
*THC content*.—23.22% by weight.
*CBD content*.—0.14% by weight.
*CBG content*.—None detected.

Terpene content:
*Method of determination*.—GC/MS as described in Zager et al. (2019, Plant Physiol. 180(4): 1877-1897).
*Beta-caryophyllene*.—6.83 mg/g.
*Limonene*.—4.56 mg/g.
*Myrcene*.—2.37 mg/g.
*Linalool*.—0.97 mg/g.
*Alpha humulene*.—0.79 mg/g.

Seeds:
*Seed length*.—5.00 mm.
*Seed width*.—3.75 mm.
*Seed color*.—#635C3F (light brown) and #342F1B (dark brown) marbled.

Resistance to abiotic stress, pests, and diseases:
*Resistance to powdery mildew*.—Resistant.

COMPARISONS TO PARENTAL AND REFERENCE VARIETIES

'D1118' differs from the female parent 'Jamaican Chocolate' (unpatented) in that 'D1118' displays larger branching angles, has darker leaf and flower coloration, has a shorter flowering period (9 weeks for 'D1118'; 12 weeks for 'Jamaican Chocolate'), displays fewer pistils, and differs in its aromatic profile relative to 'Jamaican Chocolate'.

'D1118' differs from the male parent 'Passion Fruit Haze' (unpatented) in that 'D1118' displays fewer leaves, is more vigorous, has a vastly different aroma profile, and has increased anthocyanin content in the leaves and flowers relative to 'Passion Fruit Haze'.

'D1118' differs from the reference variety 'Purple Punch' (unpatented) in that 'D1118' is more vigorous and higher yielding, differs in aromatic profile, and has a darker coloration of both flower and leaf tissue relative to 'Purple Punch'.

'D1118' differs from the reference variety 'G13' (unpatented) in that 'D1118' displays a vastly different terpene profile, has denser flower production, and displays increased anthocyanin content in its flowers relative to 'G13'.

What is claimed is:

1. A new and distinct variety of *Cannabis* plant designated 'D1118' as shown and described herein.

* * * * *